(12) United States Patent  (10) Patent No.: US 7,196,114 B2
Schoenafinger et al.  (45) Date of Patent: Mar. 27, 2007

(54) SUBSTITUTED 3-(BENZOYLUREIDO) THIOPHENE DERIVATIVES, PROCESSES FOR PREPARING THEM AND THEIR USE

(75) Inventors: Karl Schoenafinger, Alzenau (DE); Elisabeth Defossa, Idstein (DE); Erich Von Roedern, Hattersheim (DE); Dieter Kadereit, Kelkheim (DE); Andreas Herling, Bad Camberg (DE); Hans-Joerg Burger, Morristown, NJ (US); Thomas Klabunde, Frankfurt (DE); Karl-Ulrich Wendt, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 342 days.

(21) Appl. No.: 10/780,344

(22) Filed: Feb. 17, 2004

(65) Prior Publication Data

US 2004/0198742 A1  Oct. 7, 2004

Related U.S. Application Data

(60) Provisional application No. 60/487,502, filed on Jul. 15, 2003.

(30) Foreign Application Priority Data

Feb. 17, 2003 (DE) ................. 103 06 502

(51) Int. Cl.
*A61K 31/38* (2006.01)
*C07D 333/36* (2006.01)
(52) U.S. Cl. ........................ 514/447; 549/69
(58) Field of Classification Search ............ 549/69; 514/447
See application file for complete search history.

(56) References Cited

U.S. PATENT DOCUMENTS 6,221,633 B1  4/2001  Ertl et al.
6,221,897 B1  4/2001  Baringhaus et al.
6,245,744 B1  6/2001  Baringhaus et al.
6,342,512 B1  1/2002  Kirsch et al.
6,476,023 B1 *  11/2002  Cirillo et al. ............ 514/231.5
6,624,185 B2  9/2003  Glombik et al.
6,821,960 B2 *  11/2004  Jørgensen et al. .......... 514/113
6,884,812 B2  4/2005  Glombik et al.
2002/0151586 A1  10/2002  Defossa et al.

FOREIGN PATENT DOCUMENTS

| EP | 0047496 | 3/1982 |
| EP | 0 300 972 | 1/1989 |
| EP | 0 462 884 | 6/1993 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |

* cited by examiner

*Primary Examiner*—Deborah C. Lambkin
(74) *Attorney, Agent, or Firm*—Barbara E. Kurys

(57) ABSTRACT

Substituted 3-(benzoylureido)thiophene derivatives, processes for preparing them and their use The invention relates to compounds of the formula I

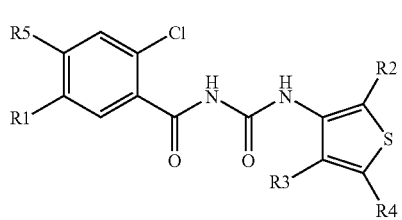

where the radicals are as defined, and their physiologically tolerated salts. The compounds are suitable, for example, as medicaments for preventing and treating type 2 diabetes.

13 Claims, No Drawings

SUBSTITUTED 3-(BENZOYLUREIDO) THIOPHENE DERIVATIVES, PROCESSES FOR PREPARING THEM AND THEIR USE

The invention relates to substituted 3-(benzoylureido) thiophene derivatives and to their physiologically tolerated salts and physiologically functional derivatives.

EP 0 300 972 describes benzoylureidothiophenes having pesticidal, specifically insecticidal and acaricidal, action.

It is an object of the invention to provide compounds which make it possible to prevent and treat diabetes mellitus. To this end, the compounds should in particular exhibit a therapeutically utilizable blood sugar-reducing action.

The invention therefore relates to compounds of the formula I

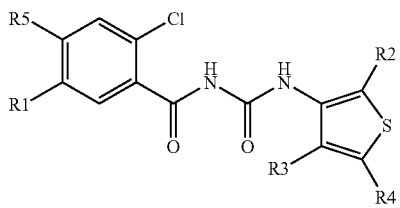

wherein

R5 is F, Cl or Br;

R1 is H, F, Cl or Br;

R2 is H, F, Cl, Br, $(C_1-C_6)$-alkyl, $CF_3$, $OCF_3$, $NO_2$, CN, O—$(C_1-C_6)$-alkyl, CO—$(C_1-C_6)$-alkyl, COOH, COO$(C_1-C_6)$-alkyl, $CONH_2$, CONH$(C_1-C_6)$-alkyl, CON$((C_1-C_6)$-alkyl$)_2$, $SO_2$—$(C_1-C_6)$-alkyl, or the A radical;

R3 is H, $(C_1-C_6)$-alkyl, COO$(C_1-C_6)$-alkyl, $SO_2$—$(C_1-C_6)$-alkyl, $(C_1-C_6)$-alkylphenyl, phenyl, $SO_2$-phenyl, wherein the phenyl rings of said $(C_1-C_6)$-alkylphenyl, phenyl and $SO_2$-phenyl groups are optionally mono- or disubstituted by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

R4 is H, $(C_1-C_6)$-alkyl, COO$(C_1-C_6)$-alkyl, $SO_2$—$(C_1-C_6)$-alkyl, $SO_2$-piperidinyl, $SO_2$-piperazinyl, $(C_1-C_6)$-alkylphenyl, wherein said $SO_2$-piperidinyl and $SO_2$-piperazinyl groups and the phenyl ring of said $(C_1-C_6)$-alkylphenyl group are optionally mono- or disubstituted by F, Cl, CN, OH, $(C_1-C_6)$-alkyl, O—$(C_1-C_6)$-alkyl, $CF_3$, $OCF_3$, COOH, COO$(C_1-C_6)$-alkyl, $CONH_2$;

A is a heterocyclic radical of the formula 2a, 2b, 2c or 3;

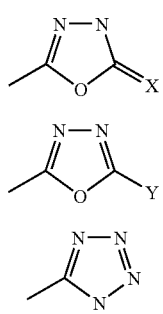

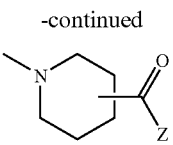

X is O or NH;

Y is OH or $NH_2$;

Z is OH, O$(C_1-C_6)$-alkyl, $NH_2$; NH$(C_1-C_6)$-alkyl or N$((C_1-C_6)$-alkyl$)_2$;

and pharmaceutically acceptable salts thereof.

Particular preference is given to compounds of the formula I wherein:

R5 is F, Cl or Br;

R1 is H or F;

R2 is H, F, Cl, Br, $(C_1-C_6)$-alkyl, $CF_3$, $OCF_3$, $NO_2$, CN, O—$(C_1-C_6)$-alkyl, CO$(C_1-C_6)$-alkyl, COOH, COO$(C_1-C_6)$-alkyl, $CONH_2$, CONH$(C_1-C_6)$-alkyl, CON$((C_1-C_6)$-alkyl$)_2$, $SO_2$—$(C_1-C_6)$-alkyl, or the A radical;

R3 is H, $(C_1-C_6)$-alkyl, COO$(C_1-C_6)$-alkyl, $SO_2(C_1-C_6)$-alkyl, $(C_1-C_6)$-alkylphenyl, phenyl, $SO_2$-phenyl, wherein the phenyl rings of said $(C_1-C_6)$-alkylphenyl, phenyl and $SO_2$-phenyl groups are optionally mono- or disubstituted by F or Cl;

R4 is H, $(C_1-C_6)$-alkyl, COO$(C_1-C_6)$-alkyl, $SO_2$—$(C_1-C_6)$-alkyl, $SO_2$-piperidinyl, $SO_2$-piperazinyl, $(C_1-C_6)$-alkylphenyl, wherein said $SO_2$-piperidinyl and $SO_2$-piperazinyl groups and the phenyl ring of said $(C_1-C_6)$-alkylphenyl group are optionally mono- or disubstituted by F, Cl, CN, OH, $(C_1-C_6)$-alkyl, O—$(C_1-C_6)$-alkyl, $CF_3$, $OCF_3$, COOH, COO$(C_1-C_6)$-alkyl or $CONH_2$;

A is a heterocyclic radical of the formula 2a, 2b or 2c;

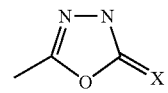

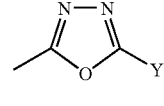

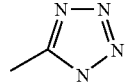

X is O or NH;

Y is OH or $NH_2$;

Z is OH;

and pharmaceutically acceptable salts thereof.

Particular preference is given to compounds of the formula I wherein:

R5 is F;

R1 is F;

R2 is COOH, COO$(C_1-C_6)$-alkyl, $CONH_2$, CONH$(C_1-C_6)$-alkyl, CON$((C_1-C_6)$-alkyl$)_2$, or the A radical;

R3 is H, $(C_1-C_6)$-alkyl, COO$(C_1-C_6)$-alkyl, $SO_2(C_1-C_6)$-alkyl, $(C_1-C_6)$-alkylphenyl, phenyl, $SO_2$-phenyl, wherein the phenyl rings of said $(C_1-C_6)$-alkylphenyl, phenyl and $SO_2$-phenyl groups are optionally mono- or disubstituted by F;

R4 is H, $(C_1-C_6)$-alkyl, $COO(C_1-C_6)$-alkyl, $SO_2$—$(C_1-C_6)$-alkyl, $SO_2$-piperidinyl, $SO_2$-piperazinyl, $(C_1-C_6)$-alkylphenyl,
   wherein said $SO_2$-piperidinyl and $SO_2$-piperazinyl groups and the phenyl ring of said $(C_1-C_6)$-alkylphenyl group are optionally mono- or disubstituted by by F or $(C_1-C_6)$-alkyl;
A is a heterocyclic radical of the formula 2a or 2b;

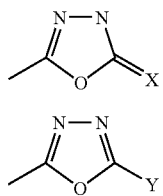

X is O or NH;
Y is OH or $NH_2$;
and pharmaceutically acceptable salts thereof.

Preference is further given to compounds of formula I in which at least one of the radicals R2, R3 and R4 is not hydrogen.

The invention relates to compounds of the formula I, in the form of their racemates, racemic mixtures and pure enantiomers, and also to their diastereomers and mixtures thereof.

The alkyl radicals in the substituents R2, R3 and R4 may be either straight-chain or branched.

When radicals or substituents can occur more than once in the compounds of the formula I, for example A, they may all each independently be defined as specified, and be the same or different.

As a consequence of their higher water solubility compared to the starting or basic compounds, pharmaceutically tolerated salts are particularly suitable for medical applications. These salts have to have a pharmaceutically tolerated anion or cation. Suitable pharmaceutically tolerated acid addition salts of the compounds according to the invention are salts of inorganic acids such as hydrochloric acid, hydrobromic acid, phosphoric acid, metaphosphoric acid, nitric acid and sulfuric acid, and also of organic acids, e.g. acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically tolerated basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts having a pharmaceutically unacceptable anion, for example trifluoroacetate, are likewise encompassed by the scope of the invention as useful intermediates for the preparation or purification of pharmaceutically tolerated salts and/or for use in nontherapeutic, for example in vitro, applications.

As used herein, the following definitions apply:
"Patient" means a warm blooded animal, such as for example rat, mice, dogs, cats, guinea pigs, and primates such as humans.
"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound of the formula I according to the invention, e.g. an ester which is able, on administration to a mammal, e.g. a human, to (directly or indirectly) form a compound of the formula I or an active metabolite thereof.

The physiologically functional derivatives also include prodrugs of the compounds according to the invention, for example as described in H. Okada et al., Chem. Pharm. Bull. 1994, 42, 57–61. Such prodrugs can be metabolized in vivo to a compound according to the invention. These prodrugs may or may not be active themselves.

The compounds according to the invention can also exist in different polymorphous forms, for example as amorphous and crystalline polymorphous forms. All polymorphous forms of the compounds according to the invention are encompassed by the scope of the invention and are a further aspect of the invention.

All references given below to "compound(s) of formula I" refer to compound(s) of the formula I as described above, and also to their salts, solvates and physiologically functional derivatives as described herein.

In this context, an aryl radical is a phenyl, naphthyl, biphenyl, tetrahydronaphthyl, alpha- or beta-tetralone, indanyl or indan-1-onyl radical.

The terms "heterocyclic ring" and "heterocyclic radical" used here relate to heteroaryl radicals and heterocycloalkyl radicals which derive from 3 to 10 membered carbon rings in which one or more carbon atoms have been replaced by one or more atoms selected from the group of oxygen, sulfur and nitrogen.

Suitable "heterocyclic rings" and "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is either 2-, 3- or 4-pyridyl. Thienyl is either 2- or 3-thienyl. Furyl is either 2- or 3-furyl.

Also included are the corresponding N-oxides of these compounds, for example 1-oxy-2-, 3- or 4-pyridyl.

Also included are singly or multiply benzofused derivatives of these heterocycles.

The compound(s) of the formula (I) can also be administered in combination with further active ingredients.

The amount of a compound of formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg and 50 mg) per day per kilogram of bodyweight, for example 3–10 mg/kg/day. An intravenous dose may, for example, be in the range from 0.3 mg to 1.0 mg/kg and may advantageously be administered as an infusion of from 10 ng to 100 ng per kilogram per minute. Suitable infusion solutions for these purposes may, for example, contain from 0.1 ng to 10 mg, typically from 1 ng to 10 mg, per milliliter. Individual doses may contain, for example, from 1 mg to 10 g of the active ingredient. Ampules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of formula I. The pharmaceutical compositions according to the invention may be produced by one of the known pharmaceutical methods which consist essentially of mixing the ingredients with pharmacologically acceptable carriers and/or excipients.

Pharmaceutical compositions according to the invention are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a certain amount of the compound of formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are prepared by uniform and homogeneous mixing of the active ingredient with a liquid and/or finely divided solid carrier, after which the product is shaped if necessary. For example, a tablet can be produced by compressing or shaping a powder or granules of the compound, optionally with one or more additional ingredients. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of formula I with a flavoring, customarily sucrose, and gum arabic or tragacanth, and pastilles which include the compound in an inert base such as gelatin and glycerol or sucrose and gum arabic.

Suitable pharmaceutical compositions for parenteral administration include preferably sterile aqueous preparations of a compound of formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. The injectable compositions according to the invention generally contain from 0.1 to 5% by weight of the active compound.

Suitable pharmaceutical compositions for rectal administration are preferably in the form of single dose suppositories. These can be prepared by mixing a compound of formula I with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters advantageously contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient is by electrotransport or iontophoresis, as described, for example, in Pharmaceutical Research, 2(6): 318 (1986).

Further useful active ingredients for combination products are as follows:

All antidiabetics mentioned in the Rote Liste 2001, chapter 12. They can be combined with the compounds of the formula I according to the invention, in particular for synergistic enhancement of the action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Antidiabetics include insulin and insulin derivatives, for example Lantus® (see www.lantus.com) or HMR 1964, fast-acting insulins (see U.S. Pat. No. 6,221,633), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In another embodiment of the invention, the compounds of the formula I are administered in combination with a cholesterol absorption inhibitor, for example, ezetimibe, tiqueside, pamaqueside.

In another embodiment of the invention, the compounds of the formula I are administered in combination with a PPAR gamma agonist, for example, rosiglitazone, pioglitazone, JTT-501, GI 262570.

In another embodiment of the invention, the compounds of the formula I are administered in combination with PPAR alpha agonist, for example, GW 9578, GW 7647.

In another embodiment of the invention, the compounds of the formula I are administered in combination with a mixed PPAR alpha/gamma agonist, for example, GW 1536, AVE 8042, AVE 8134, AVE 0847, or as described in PCT/US 11833, PCT/US 11490, DE10142734.4.

In another embodiment of the invention, the compounds of the formula I are administered in combination with a fibrate, for example, fenofibrate, clofibrate, bezafibrate.

In another embodiment of the invention, the compounds of the formula I are administered in combination with an MTP inhibitor, for example, implitapide, BMS-201038, R-103757.

In another embodiment of the invention, the compounds of the formula I are administered in combination with bile acid absorption inhibitor (see, for example, U.S. Pat. No. 6,245,744 or U.S. Pat. No. 6,221,897), for example, HMR 1741.

In another embodiment of the invention, the compounds of the formula I are administered in combination with a CETP inhibitor, for example, JTT-705.

In another embodiment of the invention, the compounds of the formula I are administered in combination with a polymeric bile acid adsorbent, for example, cholestyramine, colesevelam.

In another embodiment of the invention, the compounds of the formula I are administered in combination with an LDL receptor inducer (see U.S. Pat. No. 6,342,512), for example, HMR1171, HMR1586.

In another embodiment of the invention, the compounds of the formula I are administered in combination with an ACAT inhibitor, for example, avasimibe.

In another embodiment of the invention, the compounds of the formula I are administered in combination with an antioxidant, for example, OPC-14117.

In another embodiment of the invention, the compounds of the formula I are administered in combination with a lipoprotein lipase inhibitor, for example, NO-1886.

In another embodiment of the invention, the compounds of the formula I are administered in combination with an ATP-citrate lyase inhibitor, for example, SB-204990.

In another embodiment of the invention, the compounds of the formula I are administered in combination with a squalene synthetase inhibitor, for example, BMS-188494.

In another embodiment of the invention, the compounds of the formula I are administered in combination with a lipoprotein(a) antagonist, for example, CI-1027 or nicotinic acid.

In another embodiment of the invention, the compounds of the formula I are administered in combination with a lipase inhibitor, for example, orlistat.

In another embodiment of the invention, the compounds of the formula I are administered in combination with insulin.

In another embodiment, the compounds of the formula I are administered in combination with a sulfonylurea, for example, tolbutamide, glibenclamide, glipizide or glimepiride.

In another embodiment, the compounds of the formula I are administered in combination with a biguanide, for example, metformin.

In yet another embodiment, the compounds of the formula I are administered in combination with a meglitinide, for example, repaglinide.

In another embodiment, the compounds of the formula I are administered in combination with a thiazolidinedione, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, for example, miglitol or acarbose.

In another embodiment, the compounds of the formula I are administered in combination with an active ingredient which acts on the ATP-dependent potassium channel of the beta cells, for example, tolbutamide, glibenclamide, glipizide, glimepiride or repaglinide.

In another embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, e.g. naphthalene- 1-sulfonic acid {4-[(4-aminoquinazolin-2-ylamino)-methyl] cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In another embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In another embodiment, the other active ingredient is dexamphatamine or amphetamine.

In another embodiment, the other active ingredient is fenfluramine or dexfenfluramine.

In another embodiment, the other active ingredient is sibutramine.

In another embodiment, the other active ingredient is orlistat.

In another embodiment, the other active ingredient is mazindol or phentermine.

In another embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September–October), 18(5), 230–6.) Caromax is a carob-containing product supplied by Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of foodstuffs, for example, in bakery products or muesli bars.

It will be appreciated that any suitable combination of the compounds according to the invention with one or more of the abovementioned compounds and optionally one or more further pharmacologically active substances is regarded as being covered by the scope of protection of the present invention.

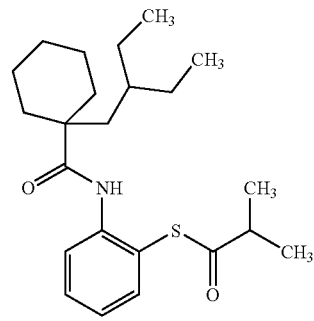

JTT-705

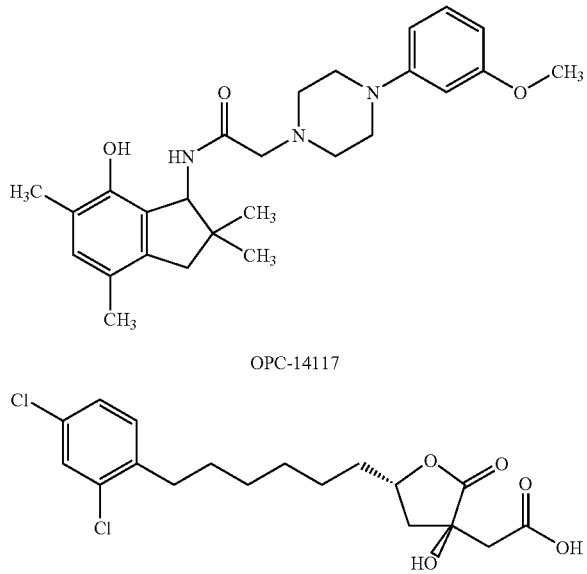

OPC-14117

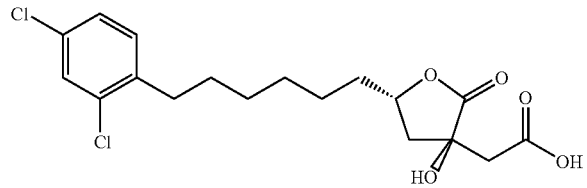

SB-204990

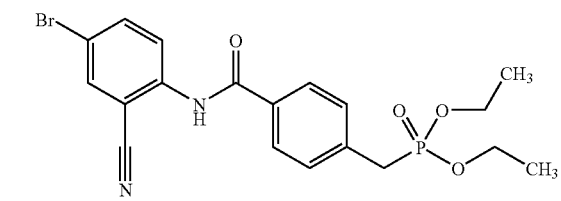

NO-1886

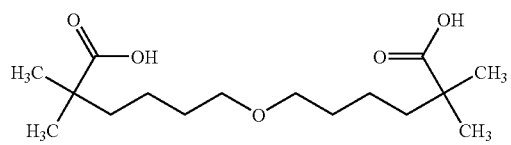

CI-1027

-continued

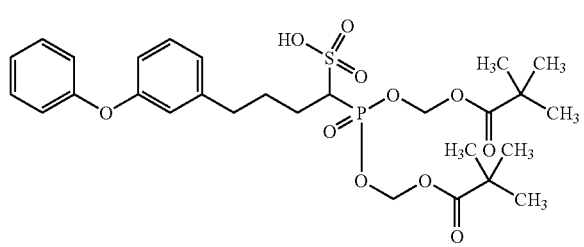

BMS-188494

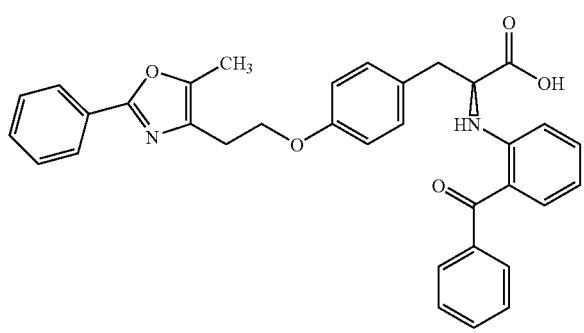

GI 262570

-continued

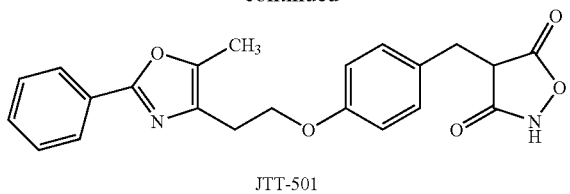

JTT-501

The citation of any reference herein should not be construed as an admission that such reference is available as "Prior Art" to the instant application.

Various publications are cited herein, the disclosures of which are incorporated by reference in their entireties.

The following examples serve to explain the invention in more detail. The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the claims.

In a similar manner, the compounds of the following examples were prepared:

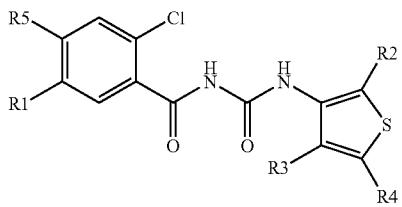

I

| Ex. | R5 | R1 | R2 | R3 | R4 | m.p. |
|---|---|---|---|---|---|---|
| 1d | F | F | 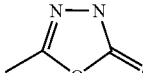 | H | H | 236.1 |
| 2c | F | F | 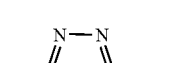 | H | H | Resin |
| 3b | F | F | COOH | H | 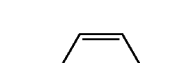 | 227.7 |
| 4d | F | F | 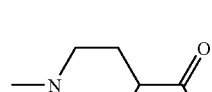 | H | 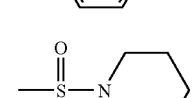 | 219.9 |
| 5 | F | F | COOMe | H | H | |
| 6 | F | F | CONH$_2$ | H | H | |
| 7 | F | F | COOMe | H | SO$_2$Me | |

-continued
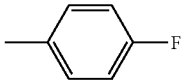
| Ex. | R5 | R1 | R2 | R3 | R4 | m.p. |
|---|---|---|---|---|---|---|
| 8 | F | F | COOMe | H |  | |
| 9 | F | F | COOMe | Me | H | |
| 10 | F | F | H | COOMe | H | |
| 11 | F | F | NO₂ | H | H | |
| 12 | F | F | COOH | SO₂Ph | H | 193.5 |
| 13 | F | F | COOH | SO₂iPr | H | 164.8 |
| 14 | F | F | COOMe | H | Ph | 208.6 |
| 15 | F | F | COMe | H | Ph | 204.8 |
| 16 | F | F | CONH₂ | H | tert-Butyl | >300 |
| 17 | F | F | CONH₂ | H | Ph | >300 |
| 18 | F | F | CONH₂ | H | 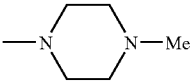 | >300 |
| 19 | F | F | 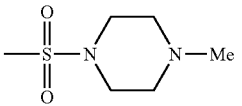 | H | 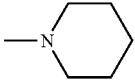 | 225.8 |
| 20 | F | F | 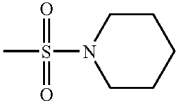 | H | 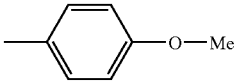 | 188.1 |
| 21 | F | F | COOH | H | Ph | 226.5 |
| 22 | F | F | CONH₂ | H | 3-Thienyl | >300 (decomp.) |
| 23 | F | F | CONH₂ | H | 2-Thienyl | >250 (decomp.) |
| 24 | F | F | CONH₂ | H | 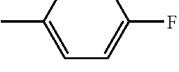 | >300 |
| 25 | F | F | —CN | H |  | >200 (decomp.) |
| 26 | F | F | COMe | H | H | 180 (decomp.) |
| 27 | F | F | CONH₂ | H | 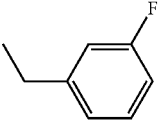 | 237.2 |
| 28 | F | F | H |  | H | |
| 29 | F | F | H | COOMe | COOMe | |
| 30 | F | F | H | Ph | H | |

-continued

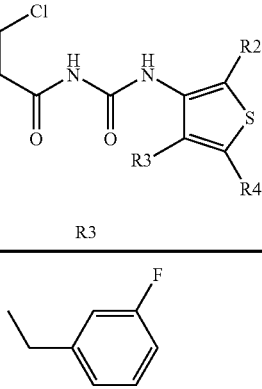

I

| Ex. | R5 | R1 | R2 | R3 | R4 | m.p. |
|-----|----|----|----|-----|-----|------|
| 31 | F | F | H | 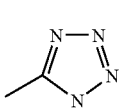 | H | |
| 32 | F | F | H | Me | H | |
| 33 | F | H | 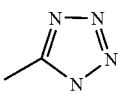 | H | H | 219.8 |
| 34 | F | F | H | H | Phenyl | 178.7 |
| 35 | F | F | COOH | H | H | 214.8 |
| 36c | F | F | 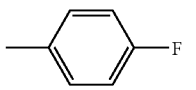 | H | 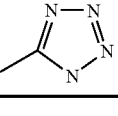 | 206.2 |
| 37 | F | H | 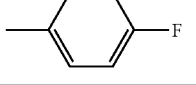 | H | 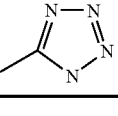 | 217.8 |

The effectiveness of the compounds was tested as follows:

Glycogen Phosphorylase a Activity Test

The effect of compounds on the activity of the active form of glycogen phosphorylase (GPa) was measured in the reverse direction by monitoring the synthesis of glycogen from glucose 1-phosphate by determining the release of inorganic phosphate. All reactions were carried out as duplicate determinations in 96-well microtiter plates (half area plates, Costar No. 3696), and the change in absorption as a consequence of the formation of the reaction product was measured at the wavelength specified below in a Multiskan Ascent Elisa Reader (Lab Systems, Finland).

In order to measure the GPa enzyme activity in the reverse direction, the conversion of glucose 1-phosphate to glycogen and inorganic phosphate was measured by the general method of Engers et al. (Engers H D, Shechosky S, Madsen N B, Can J Biochem 1970 July;48(7):746–754) with the following modifications: human glycogen phosphorylase a (for example containing 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted to a concentration of 10 μg of protein/ml with buffer T (50 mM Hepes, pH 7.0, 100 mM KCl, 2.5 mM EDTA, 2.5 mM $MgCl_2.6H_2O$) and addition of 5 mg/ml of glycogen. Test substances were prepared as a 10 mM solution in DMSO and diluted to 50 μM with buffer solution T. To 10 μl of this solution were added 10 μl of 37.5 mM glucose dissolved in buffer solution T and 5 mg/ml of glycogen, and also 10 μl of a solution of human glycogen phosphorylase a (10 μg of protein/ml) and 20 μl of 2.5 mM glucose 1-phosphate. The base value of the activity of glycogen phosphorylase a in the absence of test substance was determined by adding 10 μl of buffer solution T (0.1% DMSO). The mixture was incubated at room temperature for 40 minutes and the released inorganic phosphate was determined by means of the general method of Drueckes et al. (Drueckes P, Schinzel R, Palm D, Anal Biochem 1995 Sep. 1;230(1):173–177) with the following modifications: 50 μl of a stop solution of 7.3 mM of ammonium molybdate, 10.9 mM of zinc acetate, 3.6% of ascorbic acid, 0.9% of SDS are added to 50 μl of the enzyme mixture. After 60 minutes of incubation at 45° C., the absorption was measured at 820 nm. To determine the background absorption, the stop solution was added immediately after the addition of the glucose 1-phosphate solution in a separate reaction.

This test was carried out at a concentration of 10 μM of the test substance, in order to determine the respective inhibition of glycogen phosphorylase a by the test substance in vitro.

TABLE 2

Biological activity

| Ex. | IC-50 (μM) |
|-----|------------|
| 1d | 0.03 |
| 2c | 0.45 |
| 3b | 0.01 |

TABLE 2-continued

Biological activity

| Ex. | IC-50 (µM) |
|---|---|
| 4d | 0.11 |
| 6 | 0.70 |
| 15 | 0.17 |
| 17 | 0.03 |
| 21 | 0.01 |
| 23 | 0.05 |
| 24 | 0.04 |
| 30 | 1.40 |
| 33 | 0.08 |

It can be seen from the table that the compounds of the formula I inhibit the activity of glycogen phosphorylase a and are thus very suitable for reducing the blood sugar level.

The preparation of some examples is described in detail hereinbelow, and the remaining compounds of the formula I were obtained in a similar manner:

EXPERIMENTAL SECTION

Example 1 a) 3-(tert-Butoxycarbonylamino)thiophene-2-carboxylic hydrazide 0.4 g of hydrazine hydrate is added to a solution of 1.3 g of methyl 3-(tert-butoxycarbonylamino)thiophene-2-carboxylate in 10 ml of ethanol and the mixture is heated to reflux for 5 hours. After the volatile fractions had been removed under reduced pressure at 40° C., the remaining oil was purified by column chromatography (silica gel, eluent: methylene chloride:methanol=95:5).

Yield: 740 mg m.p.: 146.5° C.

b) tert-Butyl [2-(5-oxo-4,5-dihydro[1,3,4]oxadiazol-2-yl)thiophen-3-yl]carbamate 4 ml of a 20% toluenic phosgene solution are added dropwise to a solution of 240 mg of 3-(tert-butoxycarbonylamino)thiophene-2-carboxylic hydrazide in 5 ml of THF and the mixture is stirred at RT. After one hour, the mixture is admixed with 10 ml of water and, after brief digestion, extracted with ethyl acetate. After the ethyl acetate phase has been dried over sodium sulfate, the mixture is concentrated under reduced pressure and the remaining residue is used further without further purification.

Yield: 120 mg m.p.: 180° C.

c) 5-(3-Aminothiophen-2-yl)-3H-[1,3,4]oxadiazol-2-one hydrochloride

The mixture consisting of 100 mg of tert-butyl [2-(5-oxo-4,5-dihydro[1,3,4]oxadiazol-2-yl)thiophen-3-yl]carbamate and 5 ml of a 4 molar HCl solution in dioxane is stirred for one hour. Afterwards, the volatile fractions are removed under reduced pressure and the residue is stirred with 5 ml of tert-butyl methyl ether and the product is filtered off with suction and dried under reduced pressure.

Yield: 60 mg m.p.: 211° C.

d) 1-(2-Chloro-4,5-difluorobenzoyl)-3-[2-(5-oxo-4,5-dihydro[1,3,4]oxadiazol-2-yl)thiophen-3-yl]urea 5-(3-Aminothiophen-2-yl)-3H-[1,3,4]oxadiazol-2-one hydrochloride (30 mg) is initially charged in 3 ml of acetonitrile. The equimolar solution of 2-chloro-4,5-difluorobenzoyl isocyanate in acetonitrile is added. After 3 hours, the solid is filtered off with suction and dried under reduced pressure.

Yield: 50 mg m.p.: 236.1° C.

Example 2 a) tert-Butyl 2-(5-amino[1,3,4]oxadiazol-2-yl)thiophen-3-yl]carbamate

The solution of 192 mg of 3-(tert-butoxycarbonylamino)thiophene-2-carboxylic hydrazide in 4 ml of acetonitrile is admixed with 0.17 ml of a 5 molar cyanogen bromide solution in acetonitrile and 60 mg of potash. The mixture is stirred at RT for 4 hours, the solid is filtered off and the filtrate is concentrated under reduced pressure. The desired product is then purified by column chromatography (silica gel, eluent: methylene chloride:methanol=95:5).

Yield: 90 mg m.p.: Resin b) 5-(3-Aminothiophen-2-yl)-[1,3,4]oxadiazol-2-ylamine hydrochloride tert-Butyl 2-(5-amino[1,3,4]oxadiazol-2-yl)thiophen-3-yl]carbamate (90 mg) are added to 5 ml of 4 molar HCl solution in dioxane and the mixture is stirred at RT for one hour. After concentration under reduced pressure, the residue is stirred with tert-butyl methyl ether and the solid is filtered off with suction and dried under reduced pressure.

Yield: 60 mg m.p.: >250° (decomp.)

c) 1-[2-(5-Amino[1,3,4]oxadiazol-2-yl)thiophen-3-yl]-3-(2-chloro-4,5-difluorobenzoyl)urea 5-(3-Aminothiophen-2-yl)[1,3,4]oxadiazol-2-ylamine hydrochloride (30 mg) is initially charged in 3 ml of acetonitrile. The equimolar solution of 2-chloro-4,5-difluorobenzoyl isocyanate in acetonitrile is added and stirred at RT. After 3 hours, the solid is filtered off with suction and dried under reduced pressure.

Yield: 25 mg m.p.: Resin

Example 3 a) 3-Amino-5-(4-fluorophenyl)thiophene-2-carboxylic acid

The mixture consisting of 500 mg of methyl 3-amino-5-(4-fluorophenyl)thiophene-2-carboxylate, 160 mg of lithium hydroxide, 2 ml of water, 2 ml of THF and 2 ml of methanol is stirred at RT for 3 days. After dilution with 15 ml of water, unhydrolyzed ester is removed by extraction with ethyl acetate. The aqueous phase is adjusted to pH 5 using hydrochloric acid and stirred, and the precipitated solid is filtered off with suction and dried.

Yield: 260 mg m.p.: 145.2° C. (crude)

b) 3-[3-(2-Chloro-4,5-difluorobenzoyl)ureido]-5-(4-fluorophenyl)thiophene-2-carboxylic acid 3-Amino-5-(4-fluorophenyl)thiophene-2-carboxylic acid (50 mg) is initially charged in 3 ml of acetonitrile. The equimolar solution of 2-chloro-4,5-difluorobenzoyl isocyanate in acetonitrile is added and the mixture is stirred at RT. After 3 hours, the solid is filtered off with suction, stirred once more with methanol, filtered off with suction and dried under reduced pressure.

Yield: 46 mg m.p.: 227.7° C.

Example 4 a) 1-(5-Chloro-4-nitrothiophene-2-sulfonyl)piperidine and 1-(5-piperidino-4-nitrothiophene-2-sulfonyl)piperidine 1.7 g of piperidine are added dropwise to the solution of 2.6 g of 5-chloro-4-nitrothiophene-2-sulfonyl chloride in 8 ml of NMP with stirring and ice cooling. The mixture is stirred at RT for another 30 minutes and diluted with 30 ml of water, and the precipitate which forms is filtered off with suction after stirring. The two products are separated by column chromatography (silica gel, solvent: ethyl acetate: n-heptane=1:1).

1-(5-Piperidino-4-nitrothiophene-2-sulfonyl)piperidine: yield: 1.3 g, m.p.: 151.3° C.

1-(5-Chloro-4-nitrothiophene-2-sulfonyl)piperidine: Yield: 0.85 g m.p.: 136.4° C.

b) 1-(3-Nitro-5-piperidine-1-sulfonylthiophen-2-yl)piperidine-4-carboxylic acid The mixture of 310 mg of 1-(5-chloro-4-nitrothiophene-2-sulfonyl)piperidine, 250 mg of piperidine-4-carboxylic acid and 3 ml of NMP is stirred at 85° C. for 1 h, cooled, diluted with 15 ml of water and stirred. The precipitate is filtered off with suction, washed with water and recrystallized from isopropanol/water (4:1).

Yield: 310 mg m.p.: 165.8° C.

c) 1-[3-Amino-5-(piperidine-1-sulfonyl)thiophen-2-yl]piperidine-4-carboxylic acid The solution of 300 mg of 1-(3-nitro-5-piperidine-1-sulfonylthiophen-2-yl)piperidine-4-carboxylic acid in 20 ml of ethyl acetate is admixed with 1.0 g of tin(II) chloride and stirred at 65° C. for 8 h. After cooling, it is stirred with 30 ml of water and filtered off with suction through Celite, and the ethyl acetate phase is removed, dried and concentrated under reduced pressure. This crude product is used further without further purification.

Yield: 320 mg(crude) m.p.: Resin c) 1-[3-[3-(2-Chloro-4,5-difluorobenzoyl)ureido]-5-(piperidine-1-sulfonyl)-thiophen-2-yl]piperidine-4-carboxylic acid 1-[3-Amino-5-(piperidine-1-sulfonyl)thiophen-2-yl]piperidine-4-carboxylic acid (0.2 g of crude product) is dissolved in 2 ml of acetonitrile and admixed with the equimolar solution of 2-chloro-4,5-difluorobenzoyl isocyanate in acetonitrile, and the mixture is stirred at RT. After 3 hours, the solid is filtered off with suction and dried under reduced pressure.

Yield: 85 mg m.p.: 219.9° C.

Example 36 a) 5-(4-Fluorophenyl)-2-(1H-tetrazol-5-yl)thiophen-3-ylamine

The mixture consisting of 0.65 g of 3-amino-2-cyano-5-(4-fluorophenyl)thiophene, 7.5 ml of xylene and 0.93 g of trimethyltin azide is stirred at 130–140° C. for 3 hours. Afterwards, the mixture is concentrated at 40° C. under reduced pressure and the residue is stirred with water with the addition of 1% trifluoroacetic acid. The precipitate is filtered off with suction and dried at 40° C. under reduced pressure.

Yield: 0.6 g m.p.: 217.3° C.

c) 1-[4-(4-Fluorophenyl-2-(tetrazol-5-yl)thiophen-3-yl]-3-(2-chloro-4,5-difluorobenzoyl)urea 5-(4-Fluorophenyl)-2-(1H-tetrazol-5-yl)thiophen-3-ylamine (0.1 g) is dissolved in 2 ml of acetonitrile and admixed with the equimolar solution of 2-chloro-4,5-difluorobenzoyl isocyanate in acetonitrile and the mixture is stirred at RT. After 3 hours, the solid is filtered off with suction and dried under reduced pressure.

Yield: 73 mg m.p.: 206.2° C.

The compounds of the formula I can be prepared by reacting ureas of the formula 5 or 3-aminothiophene derivatives of the formula 6 with benzoic acid derivatives of the formula 4,

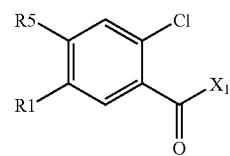

4

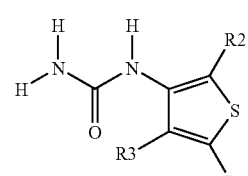

5

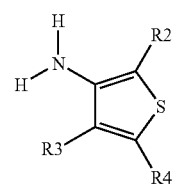

6 where R1 to R5 are each as defined above and X1 may be Cl or NCO, with acid chlorides or anhydrides or benzoyl isocyanates.

We claim:

1. A compound of formula I

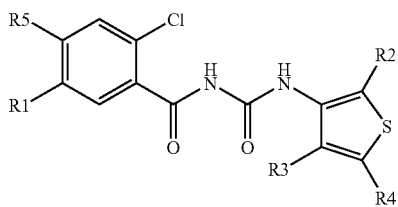

wherein

R5 is F, Cl or Br;

R1 is H, F, Cl or Br;

R2 is $CF_3$, $OCF_3$, $NO_2$, O—$(C_1$–$C_6)$-alkyl, CO—$(C_1$–$C_6)$-alkyl, COOH, $CONH_2$, $CONH(C_1$–$C_6)$-alkyl, $CON((C_1$–$C_6)$-alkyl$)_2$, $SO_2$—$(C_1$–$C_6)$-alkyl, or the A radical;

R3 is H, $(C_1$–$C_6)$-alkyl, $COO(C_1$–$C_6)$-alkyl, $SO_2$—$(C_1$–$C_6)$-alkyl, $(C_1$–$C_6)$-alkyl-phenyl, phenyl, $SO_2$-phenyl, wherein the phenyl rings of said $(C_1$–$C_6)$-alkyl-phenyl, phenyl and $SO_2$-phenyl groups are optionally mono- or disubstituted by F, Cl, CN, OH, $(C_1$–$C_6)$-alkyl, O—$(C_1$–$C_6)$-alkyl, $CF_3$, $OCF_3$, COOH, COO$(C_1$–$C_6)$-alkyl or $CONH_2$;

R4 is H, $(C_1$–$C_6)$-alkyl, $COO(C_1$–$C_6)$-alkyl, $SO_2$—$(C_1$–$C_6)$-alkyl, $SO_2$-piperidinyl, $SO_2$-piperazinyl, $(C_1$–$C_6)$-alkylphenyl, wherein said $SO_2$-piperidinyl and $SO_2$-piperazinyl groups and the phenyl ring of said $(C_1$–$C_6)$-alkylphenyl group are optionally mono- or disubstituted by F, Cl, CN, OH, $(C_1$–$C_6)$-alkyl, O—$(C_1$–$C_6)$-alkyl, $CF_3$, $OCF_3$, COOH, COO$(C_1$–$C_6)$-alkyl or $CONH_2$;

A is a heterocyclic radical of the formula 2a, 2b, 2c or 3;

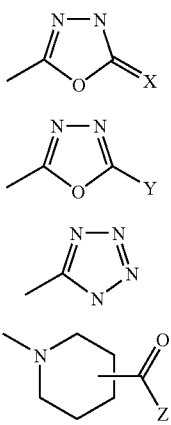

X is O or NH;

Y is OH or $NH_2$;

Z is OH, O$(C_1$–$C_6)$-alkyl, $NH_2$, $NH(C_1$–$C_6)$-alkyl or $N((C_1$–$C_6)$-alkyl$)_2$;

and pharmaceutically acceptable salts thereof.

2. The compound of claim 1, wherein

R5 is F, Cl or Br;

R1 is H or F;

R2 is $CF_3$, $OCF_3$, $NO_2$, O—$(C_1$–$C_6)$-alkyl, CO$(C_1$–$C_6)$-alkyl, COOH, $CONH_2$, $CONH(C_1$–$C_6)$-alkyl, CON$((C_1$–$C_6)$-alkyl$)_2$, $SO_2$—$(C_1$–$C_6)$-alkyl, or the A radical;

R3 is H, $(C_1$–$C_6)$-alkyl, $COO(C_1$–$C_6)$-alkyl, $SO_2(C_1$–$C_6)$-alkyl, $(C_1$–$C_6)$-alkylphenyl, phenyl, $SO_2$-phenyl, wherein the phenyl rings of said $(C_1$–$C_6)$-alkylphenyl, phenyl and $SO_2$-phenyl groups are optionally mono- or disubstituted by F or Cl;

R4 is H, $(C_1$–$C_6)$-alkyl, $COO(C_1$–$C_6)$-alkyl, $SO_2$—$(C_1$–$C_6)$-alkyl, $SO_2$-piperidinyl, $SO_2$-piperazinyl, $(C_1$–$C_6)$-alkylphenyl, wherein said $SO_2$-piperidinyl and $SO_2$-piperazinyl groups and the phenyl ring of said $(C_1$–$C_6)$-alkylphenyl group are optionally mono- or disubstituted by F, Cl, CN, OH, $(C_1$–$C_6)$-alkyl, O—$(C_1$–$C_6)$-alkyl, $CF_3$, $OCF_3$, COOH, COO$(C_1$–$C_6)$-alkyl or $CONH_2$;

A is a heterocyclic radical of the formula 2a, 2b or 2c;

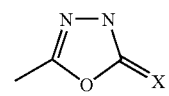

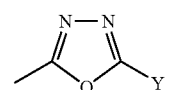

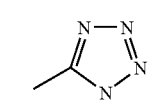

X is O or NH;

Y is OH or $NH_2$;

Z is OH;

and pharmaceutically acceptable salts thereof.

3. The compound of claim 2, wherein

R5 is F;

R1 is F;

R2 is COOH, $CONH_2$, $CONH(C_1$–$C_6)$-alkyl, CON$((C_1$–$C_6)$-alkyl$)_2$, or the A radical;

R3 is H, $(C_1$–$C_6)$-alkyl, $COO(C_1$–$C_6)$-alkyl, $SO_2(C_1$–$C_6)$-alkyl, $(C_1$–$C_6)$-alkyl-phenyl, phenyl, $SO_2$-phenyl, wherein the phenyl rings of said $(C_1$–$C_6)$-alkylphenyl, phenyl and $SO_2$-phenyl groups are optionally mono- or disubstituted by F;

R4 is H, $(C_1$–$C_6)$-alkyl, $COO(C_1$–$C_6)$-alkyl, $SO_2$—$(C_1$–$C_6)$-alkyl, $SO_2$-piperidinyl, $SO_2$-piperazinyl, $(C_1$–$C_6)$-alkylphenyl, wherein said $SO_2$-piperidinyl and $SO_2$-piperazinyl groups and the phenyl ring of said $(C_1$–$C_6)$-alkylphenyl group are optionally mono- or disubstituted by by F or $(C_1$–$C_6)$-alkyl;

A is a heterocyclic radical of the formula 2a or 2b;

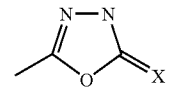

-continued

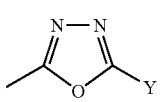
2b

X is O or NH;
Y is OH or NH$_2$;
and pharmaceutically acceptable salts thereof.

4. A pharmaceutical composition comprising a compound of claim 1 and a pharmaceutically acceptable carrier.

5. The pharmaceutical composition of claim 4 further comprising one or more additional active ingredients.

6. The pharmaceutical composition of claim 5 wherein said additional active ingredient is selected from the group consisting of antidiabetics, hypoglycemic active ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients acting on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

7. A method of reducing blood sugar comprising administering to a patient in need thereof a compound of claim 1.

8. A method of treating type II diabetes comprising administering to a patient in need thereof a compound of claim 1.

9. A method of treating lipid and carbohydrate metabolism disorders comprising administering to a patient in need thereof a compound of claim 1.

10. A method of treating arteriosclerotic symptoms comprising administering to a patient in need thereof a compound of claim 1.

11. A method of treating insulin resistance comprising administering to a patient in need thereof a compound of claim 1.

12. A process for preparing a compound of claim 1, which comprises reacting ureas of the formula 5 with benzoic acid derivatives of the formula 4

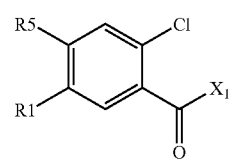
4

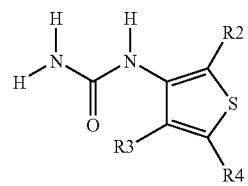
5 wherein R1 to R5 are each as defined in formula I of claim 1 and X1 is Cl.

13. A process for preparing a compound of claim 1, which comprises reacting 3-aminothiophene derivatives of the formula 6 with a benzoic acid derivative of the formula 4

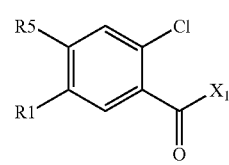
4

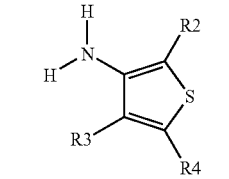
6 wherein R1 to R5 are each as defined in formula I of claim 1 and X1 is NCO.

* * * * *